(12) United States Patent
Collin et al.

(10) Patent No.: US 7,387,797 B2
(45) Date of Patent: Jun. 17, 2008

(54) **COMPOSITIONS DERIVED FROM *MODIOLUS MODIOLUS* AND METHODS FOR MAKING AND USING SAME**

(75) Inventors: Peter D. Collin, Sunset, ME (US); Thomas E. Adrian, Chicago, IL (US)

(73) Assignee: Creighton University, Omaha, NE (US)

( * ) Notice: Subject to any disclaimer, the term of this patent is extended or adjusted under 35 U.S.C. 154(b) by 474 days.

(21) Appl. No.: 10/239,345

(22) PCT Filed: Mar. 22, 2001

(86) PCT No.: PCT/US01/09192

§ 371 (c)(1),
(2), (4) Date: Dec. 30, 2002

(87) PCT Pub. No.: WO01/70130

PCT Pub. Date: Sep. 27, 2001

(65) Prior Publication Data

US 2003/0235620 A1     Dec. 25, 2003

Related U.S. Application Data

(60) Provisional application No. 60/190,967, filed on Mar. 22, 2000.

(51) Int. Cl.
*A61K 35/56* (2006.01)
*A61K 9/14* (2006.01)
(52) U.S. Cl. .................. 424/547; 424/400; 424/489; 424/520
(58) Field of Classification Search ............. 424/520, 424/547, 600, 400, 489; 514/2, 23
See application file for complete search history.

(56) References Cited

U.S. PATENT DOCUMENTS

| | | | |
|---|---|---|---|
| 4,336,247 A * | 6/1982 | Eriksen | 424/547 |
| 5,372,937 A | 12/1994 | Nilsson | |
| 6,127,166 A | 10/2000 | Bayley et al. | |
| 6,171,626 B1 * | 1/2001 | Lagos et al. | 426/324 |
| 6,596,303 B1 * | 7/2003 | Bui et al. | 424/442 |

OTHER PUBLICATIONS

Farbu et al., "Ubiquinone analysis in fish tissues and in some marine invertabrates", Comparative Biochemistry and Physiology B, 1979, vol. 63, No. 3, pp. 395-398, abstract.*
Olafsen et al., Indigenous Bacteria in Hemolymph and Tissues of Marine Bivalves at Low Temperatures, Appl. Environ, Microbiology, 1993, 59:1848-1854.*
Farbu et al., "Ubiquinone analysis in fish tissues and in some marine invertabrates", Comp Biochem Physiol, vol. 638, p. 395-397, 1979.*
Lebedev et al., "Specificity of Nitrogenous Extractive Compounds in Tissues of Metridium and Some Molluses," *Comp. Biochem. Physiol. A Comp. Physiol.*, 54(1):125-127 (1976), abstract only.

Bailey et al., "Regulation of T-Lymphocyte Mitogenesis by the Leukocyte Product 15-Hydroxy-Eicosatetraenoic Acid (15-HETE)," *Cell. Immunol.*, 67(1):112-120 (1982).
Julshamn et al., "Subcellular Distribution of Major and Minor Elements in Unexposed Molluscs in Western Norway-III. Distribution and Binding of Cadmium, Zinc, Copper, Magnesium, Manganese, Iron and Lead in the Kidney and the Digestive System of the Horse Mussel Modiolus Modiolus," *Comp. Biochem. Physiol.*, 75A(1):17-20 (1983).
Smith et al., "Eicosanoid Effects on Cell Proliferation in Virto: Relevance to Atherosclerosis," *Prostaglandins Leukotrienes Med.*, 16:1-10 (1984).
Chan et al., "Leukotriene B4 and 12-Hydroxyeicosatetraenoic Acid Stimulate Epidermal Proliferation In Vivo in the Guinea Pig," *J. Invest. Dermatol.*, 85(4):333-334 (1985).
Kragballe et al., "Increased Aggregation and Arachidonic Acid Transformation by Psoriatic Platelets: Evidence That Platelet-Derived 12-Hydroxy-Eicosatetraenoic Acid Increases Keratinocyte Dna Synthesis In Vitro," *Arch. Dermatol. Res.*, 278(6):449-453 (1986).
Nadler et al., "Specific Action of the Lipoxygenase Pathway in Mediating Angiotensin II-Induced Aldosterone Synthesis in Isolated Adrenal Glomerulosa Cells," *J. Clin. Invest.*, 80(6):1763-1769 (1987).
Setty et al., "The Mitogenic Effect of 15- and 12-Hydroxyeicosatetraenoic Acid on Endothelial Cells May Be Mediated via Diacylglycerol Kinase Inhibition," *J. Biol. Chem.*, 262(36):17613-17622 (1987).
Bandyopadhyay et al., "Proliferative Effects of Insulin and Epidermal Growth Factor on Mouse Mammary Epithelial Cells in Primary Culture. Enhancement by Hydroxyeicosatetraenoic Acids and Synergism with Prostaglandin E2," *J. Biol. Chem.*, 263(16):7567-7573 (1988).
Nolan et al., "Role of Arachidonic Acid Metabolism in the Mitogenic Response of BALB/c 3T3 Fibroblasts to Epidermal Growth," *Mol. Parmacol.*, 33(6):650-656 (1988).
Funk et al., "Molecular Cloning, Primary Structure, and Expression of the Human Platelet/Erythroleukemia Cell 12-Lipoxygenase," *Proc. Natl. Adad. Sci. USA*, 87(15):5638-5642 (1990).

(Continued)

Primary Examiner—Ruth A Davis
(74) Attorney, Agent, or Firm—Peter Rogalskyj, Esq.

(57) ABSTRACT

Disclosed are compositions which include an isolated soft tissue from *Modiolus modiolus* ("MM") and compositions which include an oil isolated from MM or a portion thereof. Also disclosed are methods of treating adenocarcinoma in a subject; methods of decreasing proliferation of adenocarcinoma cells, or of inducing apoptosis of adenocarcinoma cells, or of inducing differentiation of adenocarcinoma cells into non-cancerous cells; methods of inhibiting the activity of 5-lipoxygenase or 12-lipoxygenase or both in cells; and methods of treating a subject suffering from a disease or condition associated with excessive 5-lipoxygenase activity or 12-lipoxygenase activity or both. A process for preparing an MM extract by contacting MM or a portion thereof with a solvent under conditions effective to extract one or more materials from the MM or portion thereof is also described.

13 Claims, 4 Drawing Sheets

OTHER PUBLICATIONS

Marnet et al., "Anachidonica Acid Metabolism of Cytosolic Fractions of Lewis Lung Carcinoma Cells," *Adv. Prostaglandin Thromboxane Leukotriene Res.*, 21:895-900 (1990).

Hada et al., "Catalytic Properties of Human Platelet 12-Lipoxygenase as Compared with the Enzymes of Other Origins," *Biochim. Biophys. Acta*, 1083(1):83-93 (1991).

Rzepecki et al., "Molecular Diversity of Marine Glues: Polyphenolic Proteins From Five Mussel Species," *Molecular Marine Biology and Biotechnology*, 1(1):78-88 (1991).

Skouteris et al., "Prostaglandins E2 and F2a Mediate the Increase in c-myc Expression Induced by EGF in Primary Rat Hepatocyte Cultures," *Biochem. Biophys. Res. Comm.*, 178(3):1240-1246 (1991).

De Marzo et al., "Cloning and Expression of an Airway Epithelial 12-Lipoxygenase," *Am. J. Physiol.*, 262(2 Pt. 1):L198-L207 (1992).

Funk et al., "Characterization of Human 12-Lipoxygenase Genes," *Proc. Natl. Adad. Sci. USA*, 89(9):3962-3966 (1992).

Watanabe et al., "Molecular Cloning of a 12-Lipoxygenase cDNA from Rat Brain," *Eur. J. Biochem.*, 212(2):605-612 (1993).

Dethlefsen et al., "Arachidonic Acid Metabolites in bFGF-, PDGF-, and Serum-Stimulated Vascular Cell Growth," *Exp. Cell. Res.*, 212(2):262-273 (1994).

Lysz et al., "12(S)-Hydroxyeicosatetraenoic Acid Regulates DNA Synthesis and Protooncogene Expression Induced by Epidermal Growth Factor and Insulin in Rat Lens Epithelium," *Cell Growth Differ.*, 5(10):1069-1076 (1994).

Fesus et al., "Probing the Molecular Program of Apoptosis by Cancer Chemopreventive Agents," *J. Cell. Biochem. Suppl.*, 22:151-161 (1995).

Freire-Moar et al., "Cloning and Characterization of a Murine Macrophage Lipoxygenase," *Biochim. Biophys. Acta*, 1254(1):112-116 (1995).

Lotan, "Retinoids and Apoptosis: Implications for Cancer Chemoprevention and Therapy," *J. Natl. Cancer Inst.*, 87(22):1655-1657 (1995).

van Zandwijk, "N-acetylcysteine (NAC) and Glutathione (GSH): Antioxidant and Chemopreventive Properties, with Special Reference to Lung Cancer," *J. Cell Biochem. Suppl.*, 22:24-32 (1995).

Database BIOSIS on STN, Accession No. 1976:172502 (1976) (Abstract only).

Database BIOSIS on STN, Accession No. 1983:326909 (1993) (Abstract only).

Database BIOSIS on STN, Accession No. 1995:126311 (1995) (Abstract only).

Database BIOSIS on STN, Accession No. 1994:97546142 (1994), entire document.

Carbon Isotope Compositions of Fatty Acids in Mussels from Newfoundland Estuaries, *Estuarine, Coastal and Shelf Science*, 39:261-272 (1994).

* cited by examiner

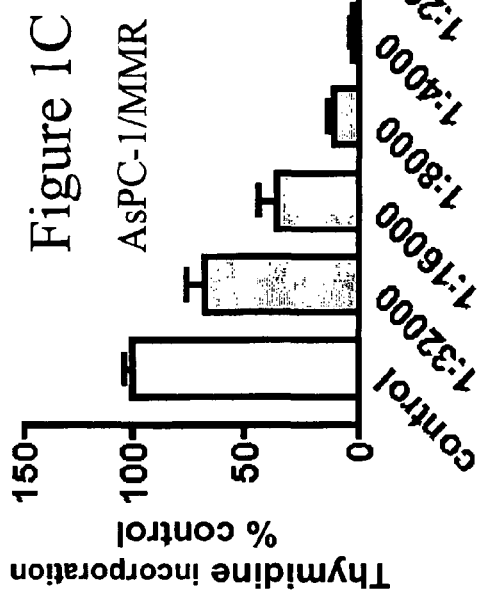
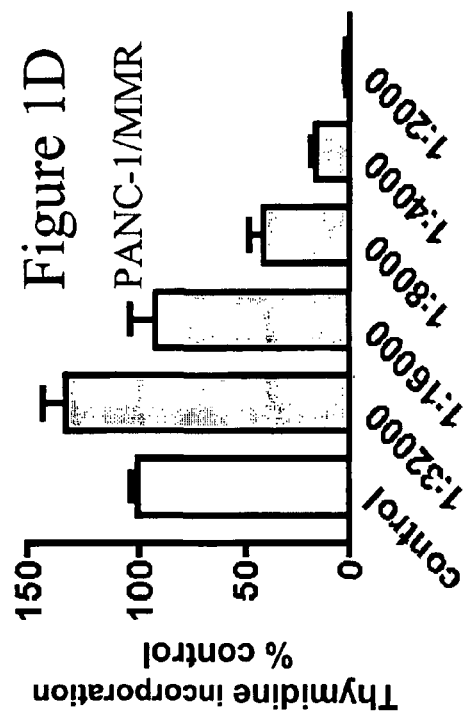
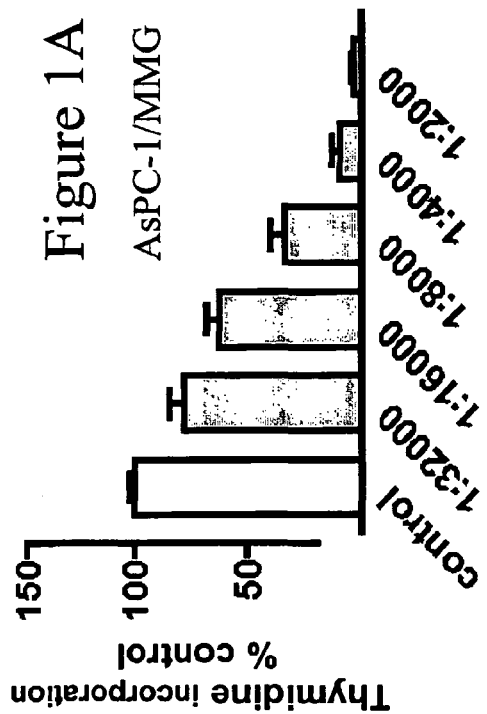
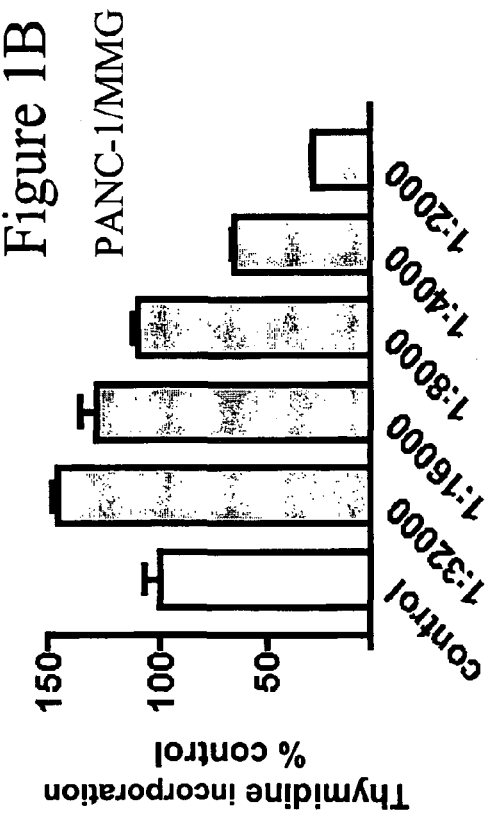

AsPC-1
control

AsPC-1
MMR (1:800)

AsPC-1
MMG (1:400)

PANC-1
control

PANC-1
MMR (1:800)

PANC-1
MMG (1:400)

AsPC-1
control

AsPC-1
MMR

AsPC-1
MMG

PANC-1
control

PANC-1
MMR

PANC-1
MMG

COMPOSITIONS DERIVED FROM *MODIOLUS MODIOLUS* AND METHODS FOR MAKING AND USING SAME

The present application is a 371 of International Patent Application No. PCT/US01/09192, filed Mar. 22, 2002, which claims the benefit of U.S. Provisional Patent Application Ser. No. 60/190,967, filed Mar. 22, 2000, which is hereby incorporated by reference.

FIELD OF THE INVENTION

The subject invention is directed to compositions containing *Modiolus modiolus* and extracts thereof, to compositions containing same, and to methods for making and using these extracts and compositions.

BACKGROUND OF THE INVENTION

A number of diseases and conditions are believed to be associated with excessive 5- and/or 12-lipoxygenase activity. These include inflammation, arthritis, multiple sclerosis, diabetes, and coronary disease, as well as cancers, for example of the prostate, colon, pancreas, and lung.

Inflammation represents a cascade of physiological and immunological reactions that nature has designed as the first cellular response to noxious stimuli in an effort to localize toxic materials or prevent tissue injury. Clinically, inflammation is a primary disease under acute conditions or is a manifestation of underlying pathophysiological abnormalities in chronic disease, characterized by classic signs of redness, pain, swelling, and loss of function. Inflammatory diseases are a significant cause of morbidity and mortality in humans.

Arthritis is a disease that results in degradation and degeneration of the articular cartilage. The major symptoms of arthritis are pain, stiffness, crackling, and enlargement, and deformities of the affected joints, and, in some cases, these symptoms can be accompanied by inflammation and swelling of the joints. To ease the pain associated with arthritis, millions of people ingest daily high doses of non-steroidal anti-inflammatory drugs ("NSAIDs"), such as ibuprofen. Unfortunately, NSAIDs irritate the stomach and the intestines in many people causing ulcers and bleeding. It has been reported in the Archives of Internal Medicine that ulcers and gastrointestinal bleeding caused by NSAIDs lead to as many as 20,000 deaths each year.

Pancreatic cancer is one of the most enigmatic and aggressive malignant diseases facing oncologists (Parker et al., "Cancer Statistics. 1996," *CA Cancer J. Clin.*, 46:5-27 (1996) ("Parker")). It is now the fourth leading cause of cancer death in both men and women in the United States, and the incidence of this disease has significantly increased over the past 20 years (Parker; Trede et al., "Survival After Pancreaticoduodenectomy: 118 Consecutive Resections Without an Operative Mortality," *Ann. Surg.*, 211:447-458 (1990); Cameron et al., "One Hundred and Forty-five Consecutive Pancreaticoduodenectomies Without Mortality," Ann. Surg.,217: 430-438 (1993); Horward, "Pancreatic Adenocarcinoma," *Curr. Prob. in Cancer,* 20:286-293 (1996) ("Horward"); Poston et al., *Gut. Biology of Pancreatic Cancer,* 32:800-812 (1991) ("Poston"); and Black et al., "Treatment of Pancreatic Cancer: Current Limitations, Future Possibilities," *Oncology,* 10:301-307 (1996) ("Black")). Pancreatic cancer is responsible for 27,000 deaths per year in the United States. Because of lack of early diagnosis and poor therapeutic responsiveness of pancreatic cancer, less than 2% of patients survive beyond five years, and the median expectation of life after diagnosis of pancreatic cancer is less than 6 months (Horward; Poston; and Black).

Colonic cancer is the second most common form of cancer in the United States (Doll et al., "Mortality in Relation to Smoking: 20 Years' Observations on Male British Doctors," *BMJ,* 2:1525-153.6 (1976); Hruban et al., "Molecular Diagnosis of Cancer and Micrometastases," *Adv. Anat. Pathol.,* 5:175-178 (1998) ("Hruban"); Figueredo et al., "Adjuvant Therapy for Stage II Colon Cancer After Complete Resection. Provincial Gastrointestinal Disease Site Group," *Cancer Prev. Control,* 1:379-92 (1997) ("Figueredo"); Ness et al., "Outcome States of Colorectal Cancer: Identification and Description Using Patient Focus Groups," *Am. J. Gastroenterol.,* 93:1491-7 (1998) ("Ness"); Trehu et al., "Cost of Screening for Colorectal Cancer: Results of a Community Mass Screening Program and Review of Literature," *South Med. J.,* 85:248-253 (1992); and Wingo et al., "Cancer Statistics," *CA Cancer J. Clin.,* 45:8-30 (1995) ("Wingo")). Colonic cancer occurs in more than 138,000 patients and is responsible for more than 55,000 deaths in the United States each year (Wingo). Up to 70% of patients with colonic cancer develop hepatic metastasises by the time of death, indicating that non-detectable micro-metastases are present at the time of surgery (Hruban; Figueredo; and Ness). Furthermore, metastatic cancer is often not responsive to standard chemotherapeutic regimens, resulting in treatment failure (Figueredo and Ness). The overall response of advanced or non-resectable colorectal cancer patients to chemotherapeutic agents varies from 26 to 44 percent. For example, less than one third of colorectal cancer patients with liver metastases respond to treatment with agents such as 5-FU and leucovorin (Id.).

Breast cancer has the highest incidence of any cancer in women with the diagnosis being made in more than 275,000 per year in the USA (Richards et al., "Influence of Delay on Survival in Patients with Breast Cancer: A Systematic Review," *Lancet,* 353:1119-26 (1999); Norton, "Adjuvant Breast Cancer Therapy: Current Status and Future Strategies—Growth Kinetics and the Improved Drug Therapy of Breast Cancer," *Semin. Oncol.,* 26:1-4 (1999); Morrow et al., "Current Controversies in Breast Cancer Management," *Curr. Probl. Surg.,* 36:163-216 (1999); and Ruppert et al., "Gene Therapy Strategies for Carcinoma of the Breast," *Breast Cancer Res. Treatment,* 44:93-114 (1997)). Even though five year survival has increased to more than 80%, more than 77,000 women still die from this disease each year (Id.).

Accordingly, there continues to be a need for agents and methods for treating pancreatic, colonic, and breast cancer as well as diseases and conditions that are believed to be associated with the inappropriate expression and/or activity of 5- and/or 12-lipoxygenases. The present invention is directed, in part, to meeting these needs.

SUMMARY OF THE INVENTION

The present invention relates to a composition which includes an isolated soft tissue from *Modiolus modiolus* ("MM").

The present invention also relates to a composition which includes an oil isolated from MM or a portion thereof.

The present invention also relates to a method of treating adenocarcinoma in a subject. The method includes administering a composition which includes an MM soft tissue or an extract thereof to the subject.

The present invention also relates to a method of decreasing proliferation of adenocarcinoma cells, or of inducing apoptosis of adenocarcinoma cells, or of inducing differentiation of adenocarcinoma cells into non-cancerous cells. The method includes contacting a sample which includes adenocarcinoma cells with a composition comprising an MM soft tissue or an extract thereof.

The present invention also relates to a method of inhibiting 5-lipoxygenase activity or 12-lipoxygenase activity or both in cells. The method includes contacting a sample which includes the cells with a composition comprising an MM soft tissue or an extract thereof under conditions effective to inhibit 5-lipoxygenase activity or 12-lipoxygenase activity or both in the cells.

The present invention also relates to a method of treating a subject suffering from a disease or condition associated with excessive 5-lipoxygenase activity or 12-lipoxygenase activity or both. The method includes administering a composition which includes an MM soft tissue or an extract thereof to the subject.

The present invention also relates to a process for preparing an MM extract. The process includes contacting MM or a portion thereof with a solvent under conditions effective to extract one or more materials from the MM or portion thereof.

BRIEF DESCRIPTION OF THE DRAWINGS

FIGS. 1A-1D are bar graphs showing the effects of different concentrations of two MM oil extracts on thymidine incorporation in pancreatic cancer cell lines AsPC-1 (FIGS. 1A and 1C) and PANC-1 (FIGS. 1B and 1D).

FIGS. 2B and 2C show the morphological changes induced by each of two different MM oil extracts in AsPC-1 pancreatic cancer cells relative to control (FIG. 2A). FIGS. 2E and 2F show the morphological changes induced by each of two different MM oil extracts in PANC-1 pancreatic cancer cells relative to control (FIG. 2D).

DETAILED DESCRIPTION OF THE INVENTION

Figure 2A:
FIGS. 2A-2F are phase contrast micrograph images.

The present invention relates to a composition which includes an isolated soft tissue from *Modiolus modiolus* ("MM").

As used herein, "*Modiolus modiolus*" is an organism belonging to the *modiolus* species in the *Modiolus* genus in the Mytilidae family in the Mytiloidea superfamily in the Bivalvia class in the Mollusca phylum in the Animilia kingdom. It is described and characterized in, for example, Anwar, et al., *J. Mar. Biol. Assoc. U. K.*, 70:441-457 (1990); Brown et al., "*Modiolus modiolus* (L.)—An Autoecological Study," pp. 93-100 in Keegan et al., eds., *Biology of Benthic Organisms. Proceedings of the 11th European Symposium on Marine Biology. Galway. Ireland* (1976), Oxford: Pergammon Press (1977); and Navarro et al., *Marine Ecology Progress Series*, 138:135-148 (1996), which are hereby incorporated by reference.

MM individuals grow to a size of about 150-180 mm. They can be found in the Atlantic Ocean (e.g., from Long Island to Maine to Newfoundland to Ireland and Sweden; in the Baltic Sea (e.g., from Norway and Sweden to Denmark and Belgium), and in the Pacific Ocean (e.g., from the Bering Sea to southern California). Typically, they live in quiet bays, in intertidal regions, or in waters of up to 200 m depth. In bay environments, they are generally buried in soft, gravely mud or sand or attached to rocks or other structures. They can be harvested from the waters in which they live using methods well known to those skilled in the art, such as by using drags.

The anatomy of MM is well known. Briefly, it includes a shell that is secreted by a soft body mass called the "mantle." The mantle lies immediately beneath the interior surface of the shell and surrounds the soft tissues of MM. As used herein, MM soft tissues are meant to include MM foot, heart, stomach, kidney, gonad, liver (a green-colored organ also commonly referred to as the "digestive gland"), mouth, labial palps (generally present as two pairs), gills (generally present as two pairs), and combinations thereof.

As used herein, an isolated soft tissue from MM is one which is substantially free of at least one other MM component with which it naturally occurs. For the purposes of the present invention, material X is considered to be "substantially free" of material Y when material X contains less than about 10% (e.g., less than about 5%, less than about 2%, less than about 1%, and/or less than about 0.5%) by weight of material Y. For example, as indicated above, naturally occurring MM contains a shell, a mantle, and soft tissues. Accordingly, MM soft tissues which are substantially free of the MM shell, substantially free of the MM mantle, or substantially free of MM shell and mantle would be considered to be isolated MM soft tissues. Also, as indicated above, naturally occurring MM contains the following soft tissues: foot, heart, stomach, kidney, gonad, liver, mouth, two pairs of labial palps, and two pairs of gills. Accordingly, MM soft tissues which are substantially free of one or more of these soft tissue components would be considered to be isolated MM soft tissues (irrespective of whether shell and/or mantle are present).

Illustratively, the composition of the present invention can contain MM liver and be substantially free of MM foot, heart, stomach, kidney, gonad, mouth, labial palps, and gills. Alternatively, the composition of the present invention can contain an MM soft tissue selected from the group consisting of MM foot, heart, stomach, kidney, gonad, mouth, labial palps, gills, and combinations thereof and be substantially free of MM liver.

"Composition", as used herein, is meant to include one-component compositions (e.g., as in the case where the composition contains only MM liver) as well as two- or multi-component compositions (e.g., as in the case where the composition contains MM liver and one or more other MM soft tissues; as in the case where the composition contains MM liver and one or more other components which are not found in naturally occurring MM; or as in the case where the composition contains MM liver, one or more other MM soft tissues, and one or more other components which are not found in naturally occurring MM.

As indicated above, the composition of the present invention can optionally contain components which are not found in naturally occurring MM. Examples of such components which are not found in naturally occurring MM include, for example, pharmaceutically and/or nutriceutically acceptable excipients (discussed further below) and materials commonly used in the food processing industry, such as proteins, sugars and other carbohydrates, extenders, fillers, preservatives, and the like. The weight ratio of these excipients and materials to the isolated MM soft tissue is not particularly critical to the practice of the present invention and can range from about 10000:1 to about 1:100 (e.g., from about 1000:1 to about 1:100, from about 100:1 to about 1:100, from about 50:1 to about 1:50, from about 20:1 to about 1:20, from about 10:1 to about 1:10, from about 10000:1 to about 10:1, and/or from about 1000:1 to about 50:1).

The isolated soft tissue from MM contained in the composition of the present invention can be present in its naturally occurring form, or it can be present in a processed form. Examples of processed forms include minced, crushed, pureed, homogenized, ground, dried, freeze-dried, salt-cured, cooked, (e.g., baked, steamed, poached, broiled, pan-fried, deep fried, etc.), and the like.

Methods for making the compositions of the present invention are, generally, conventional. For example, after harvesting the MM (for example, as described above), the shells can be opened using any conventional method for opening the shells of shellfish (e.g., hand de-shelling, machine de-shelling, etc., with or without heating). Typically, the shells and the mantle are discarded, and the resulting isolated soft tissues are then processed. This processing can further include separating one or more of the various soft tissues (e.g., one or more of the foot, heart, stomach, kidney, gonad, liver, mouth, labial palps, and gills) from the remainder of the soft tissues, for example using a knife or a razor. The retained soft tissues can then optionally be minced, crushed, pureed, homogenized, ground, dried (air-dried, heat-dried, etc.), freeze-dried, salt-cured, and/or cooked, according to conventional procedures well known to those skilled in the art. In some applications, it may be desirable to cook the isolated MM soft tissue prior to separating the various soft tissues from each other, and, in some applications, it may be preferable to dry or freeze-dry the isolated soft tissue from MM and then to grind the resulting solid into a powder form. Other components of the desired final composition can be added to the isolated MM soft tissue composition prior to, during, and/or subsequent to processing.

The above-discussed compositions can be used directly in the methods described below, or they can be used to make oils or other extracts, to which the present invention also relates, as discussed below.

The present invention, in another aspect thereof, relates to a composition which includes an oil isolated from MM or from portions thereof (e.g., from one or more of the MM soft tissues). As used herein, "oil" is meant to include materials (e.g., liquids, viscous syrups, gums, resins, etc.) which are soluble in at least one organic solvent and which are insoluble or sparingly soluble in water. For example, the oil can be produced by contacting MM or a portion thereof with a solvent under conditions effective to extract one or more materials from the MM or portion thereof. Illustratively, after harvesting the MM as described above, the entire MM specimen can be crushed to produce a mixture of shell, mantle, and soft tissue, and the extraction can be carried out on this mixture. Preferably, however, the MM shell and mantle are separated from its soft tissue, for example, using the methods discussed above, prior to extraction. Also, prior to extraction, the MM soft tissue can be further processed. For example, the soft tissue can optionally be minced, crushed, pureed, homogenized, ground, dried (air-dried, heat-dried, etc.), freeze-dried, salt-cured, and/or cooked, according to conventional procedures well known to those skilled in the art. In some applications, it may be preferable to dry or freeze-dry the isolated soft tissue from MM and then to grind the resulting solid into a powder form prior to extraction.

As discussed more fully below, different soft tissues are believed to yield different oils. Accordingly, in some cases it may be desirable to extract oils from fewer than all of the MM soft tissues (i.e., from one or more (but not all) of the MM foot, heart, stomach, kidney, gonad, liver, mouth, labial palps, and gills). This can be achieved by separating one or more of the various soft tissues (e.g., one or more of the foot, heart, stomach, kidney, gonad, liver, mouth, labial palps, and gills) from the remainder of the soft tissues, for example using a knife or a razor. As indicated above, in some applications, it may be desirable to cook the MM soft tissue prior to separating the various soft tissues from each other.

Thus, in one illustrative example, the extraction process can be carried out on the combination of MM foot, heart, stomach, kidney, gonad, liver, mouth, labial palps, gills, and combinations thereof. In another illustrative example, the extraction process can be carried out on MM liver which is substantially free of MM foot, heart, stomach, kidney, gonad, mouth, labial palps, and gills. In still another illustrative example, the extraction process can be carried out on an MM soft tissue that is selected from the group consisting of MM foot, heart, stomach, kidney, gonad, mouth, labial palps, gills, and combinations thereof but which is substantially free of MM liver.

Suitable solvents for extraction include alcohol solvents (e.g., methanol, ethanol, n-propanol, isopropanol, butanol, and combinations thereof); ketone solvents (e.g., acetone, methyl ethyl ketone, cyclohexanone, and combinations thereof); ether solvents (e.g., diethyl ether, methyl ethyl ether, tetrahydrofuran, ethoxyethanol, and combinations thereof); hydrocarbon solvents, which may be linear, branched, or cyclic (e.g., propane and/or butane (under pressure), pentanes, hexanes, cyclohexane, petroleum ether, and combinations thereof); halohydrocarbon solvents, including chlorohydrocarbons, fluorohydrocarbons, fluorochlorohydrocarbons (e.g. methylene chloride, chloroform, tetrachloroethylene, dichlorodifluoromethane, chlorobenzene, and combinations thereof); aromatic solvents (e.g., benzene, toluene, xylene, and combinations thereof); carbon dioxide (supercritical); and combinations of these and other solvents.

Extraction can be carried out using any suitable procedure. Generally, the MM or a portion thereof (unprocessed or processed by one or more of the methods described above) is contacted with the solvent under conditions effective to extract one or more materials from the MM or portion thereof. Contacting can be carried out while the solvent is in liquid or vapor phase. Generally, the extraction process is accelerated by agitating (e.g., by mixing, stirring, shaking, refluxing, etc.) the MM or portion thereof while it is in contact with the solvent and/or by conducting the extraction at elevated temperatures (e.g., from just above room temperature to the boiling point of the solvent). The progress of the extraction process can be monitored by taking samples of the solvent at various times during the process and assessing the amount of oil in the samples, e.g., by visible or UV absorption spectroscopy, turbidity measurements, thin-layer chromatography, etc.). The extraction can be carried out for from about 1 hour to about 4 days or until the amount of oil in the solvent ceases to increase over time. Continuous-feed extraction processes can also be employed.

Illustratively, flesh from MM is separated into green and rose-colored parts, corresponding to the liver and other organs, respectively, and the white striated muscle bands attached to the shell and bysus thread are removed along with the white retractor muscle. Separated flesh is then freeze-dried by methods known in the arts and finely divided. Finely divided freeze-dried MM (e.g., approximately 500 kg) is placed in a $CO_2$ high pressure reaction vessel at an industrial $CO_2$ extraction plant (e.g., one known to the hops and de-caffeinated coffee industries) and subjected to pressures of between about 1000 psi and about 9500 psi, such as of between about 2000 psi and 9500 psi and/or of about 4500 psi; at temperatures of between about 30° C. and about 655° C., such as of between about 30° C. and about 200° C., of between about 35° C. and about 80° C., and/or of about 45° C.; for from about 0.5 to about 8 hours, preferably for about 1 hour. MM oil thus extracted can then be stabilized with mixed tocopherols at about 2% or with mixed flavenoids (such as with an alcohol extract of baicaleinsis known in the industry as baicalein or baicalin). Alternatively, the oil extract can be stabilized with an additional lipoxygenase inhibitor known as an alcohol extract of boswellia serrata. Using this method, the recovery of oil from MM is typically between about 3 and about 10%. The remaining dry powder of MM can be used as a protein and glycosaminoglycan supplement, or it can be further extracted of its glycosaminoglycan content (e.g., by methods known in the polysaccharide extraction arts) and incorporated into human and/or animal feed as a nutritive supplement.

Extraction of the more polar compounds (e.g., pigments, such as chlorophyll and carotenoids) from MM can be accomplished by the addition of ethanol, acetone, or other polar solvents as is known in the $CO_2$ extraction arts. Additionally, polar species of MM oil can be preferentially extracted separately from the non-polar extraction procedure above, by subjecting the MM tissue to the pure $CO_2$ extraction, thus retrieving all the non-polar lipid species, and subsequently subjecting the remaining tissue to a $CO_2$ extraction at the same or similar pressures and temperatures but with the addition of the polar solvents. The polar solvents can be mixed with the MM powder, or they can be pumped as a co-solvent with the supercritical liquid $CO_2$.

Once extraction is complete, the extraction solvent (containing the extracted materials) is typically (but optionally) separated from the remaining MM soft tissue. This can be achieved, for example, by filtration, by centrifugation, by settling and decanting, or by combinations of these and other known methods for separating solids from liquids. The solids are then typically discarded or re-extracted, and the solvent is typically (but optionally) separated from the extracted materials, for example, by evaporation at ambient or reduced pressure with or without heating. The resulting material, typically an oil, is collected.

As indicated above, the present invention relates to a composition which includes an oil isolated from MM. The composition can be a one-component composition, as in the case where the compositions contains only the oil. Alternatively, the composition can be a two-component composition, for example, as in the case where the composition contains the oil dispersed or dissolved in the solvent with which it was extracted; as in the case where the composition contains the oil dispersed or dissolved in another liquid dispersant or solvent; and as in the case where the composition contains the oil dispersed on or in an inert solid carrier (e.g., talc, cellulose, etc.). Still alternatively, the composition can be a multi-component composition, for example, as in the case where the composition contains the oil dispersed or dissolved in a mixture of liquid dispersants and/or solvents; and as in the case where the composition contains the oil dispersed on or in a mixture of inert solid carriers (e.g., talc, cellulose, etc.). The compositions can optionally include pharmaceutically and/or nutriceutically acceptable excipients (discussed further below) and materials commonly used in the food processing industry, such as proteins, sugars and other carbohydrates, extenders, fillers, preservatives, and the like. The weight ratio of these excipients and materials to the MM oil is not particularly critical to the practice of the present invention and can range from about 10000:1 to about 1:100 (e.g., from about 1000:1 to about 1:100, from about 100:1 to about 1:100, from about 50:1 to about 1:50, from about 20:1 to about 1:20, from about 10:1 to about 1:10, from about 10000:1 to about 10:1, and/or from about 1000:1 to about 50:1).

The present invention, in yet another aspect thereof, relates to a method of decreasing proliferation of adenocarcinoma cells, or of inducing apoptosis of adenocarcinoma cells, or of inducing differentiation of adenocarcinoma cells into non-cancerous cells. The method includes contacting a sample which includes adenocarcinoma cells with a composition comprising an MM soft tissue or an extract thereof. Examples of MM soft tissue suitable for use in the practice of this aspect of the present invention include the above-discussed isolated MM soft tissues and compositions containing such isolated MM soft tissues. Examples of MM extracts include oils isolated from MM, such as those discussed above. The meaning of the terms "proliferation", "apoptosis", and "differentiation" are readily understood in the art. Illustrative methods for assaying for proliferation, apoptosis, or differentiation are provided in the examples which follow and are also described in applicant's copending U.S. patent application Ser. No. 09/111,343, which is hereby incorporated by reference. "Adenocarcinoma cells", as used herein, are meant to include cancerous epithelial cells, such as prostate cancer cells, lung cancer cells, stomach cancer cells, breast cancer cells, pancreatic cancer cells, and colon cancer cells. The methods of the present invention can be practiced in vitro or in vivo.

More particularly, the method of the present invention can be used in vivo to treat adenocarcinomas, such as prostate cancer, lung cancer, stomach cancer, pancreatic cancer, breast cancer, and colon cancer. In the case where the method of the present invention is carried out in vivo, for example, where the adenocarcinoma cells are present in a human subject, contacting can be carried out by administering a therapeutically effective amount of the MM soft tissue or extract thereof to the human subject, for example, by directly injecting the MM soft tissue or extract thereof into a tumor. Details with regard to administering the MM soft tissues or extracts thereof in accordance with the method of the present invention are described below.

The present invention, in another aspect thereof, relates to a method of treating adenocarcinomas, such as prostate cancer, lung cancer, stomach cancer, breast, pancreatic cancer, colon cancer, esophageal cancer, uterine cancer, ovarian cancer, or other cancers involving epithelial cells. As used in the context of this aspect of the present invention, "treating" is meant to include preventative treatments, for example in a subject at risk for adenocarcinoma, as well as treatments designed to slow, stop, or reverse progression of the adenocarcinoma in subjects exhibiting clinical symptoms of adenocarcinoma. The method includes administering, to the subject, an MM soft tissue or extract thereof.

Suitable subjects include, for example mammals, such as rats, mice, cats, dogs, horses, monkeys, and humans. Suitable human subjects include, for example, those which have previously been determined to be at risk of having prostate cancer, lung cancer, stomach cancer, pancreatic cancer, colon cancer, and/or breast cancer and those who have been diagnosed as having prostate cancer, lung cancer, stomach cancer, pancreatic cancer, colon cancer, and/or breast cancer. Preferably, the subject suffers from only one of these types of cancers, for example, from only pancreatic cancer.

In subjects who are determined to be at risk of having adenocarcinoma, the above-identified MM soft tissues or extracts thereof are administered to the subject, preferably under conditions effective to decrease proliferation and/or induce apoptosis and/or induce differentiation of the adenocarcinoma cells in the event that they develop. Such preventive (which is not used in the absolute 100% sense) therapy can be useful in high risk individuals as long as the adverse side effects of the administration of these MM soft tissues or extracts thereof are outweighed by the potential benefit of prevention.

It should be noted that the above-described methods for treating adenocarcinoma may operate via a mechanism which involves a reduction in 5- and/or 12-lipoxygenase activity. However, this need not be the case, and this aspect of the present invention is not, in any way, intended to be limited by the mechanism by which the MM soft tissue or extract thereof operate.

Any of the MM soft tissues or extracts thereof described above can be used in the treatment methods of the present invention. For example, MM soft tissues or extracts thereof may be administered alone or in combination with compatible carriers as a composition. Compatible carriers include suitable pharmaceutical and/or nutriceutical carriers or diluents. The diluent or carrier ingredients should be selected so that they do not diminish the therapeutic effects of the MM soft tissues or extracts thereof.

The compositions herein may be made up in any suitable form appropriate for the desired use. Examples of suitable dosage forms include oral, parenteral, or topical dosage forms.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate. Dosage forms for oral administration can also be formulated as food preparations using materials which are conventionally used in the food processing industry, such as proteins, sugars and other carbohydrates, extenders, fillers, preservatives, and the like.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

Suitable topical dosage forms include gels, creams, lotions, ointments, powders, aerosols and other conventional forms suitable for direct application of medicaments to skin or mucous membranes. Topical ointments, pastes, creams, and gels can include, in addition to the active MM soft tissues and/or extracts thereof, customary excipients, for example animal and vegetable fats, waxes, paraffins, starch, tragacanth, cellulose derivatives, polyethylene glycols, silicones, bentonites, silicic acid, talc, and zinc oxide, or mixtures of these substances. Topical powders and sprays can include, in addition to the active MM soft tissues and/or extracts thereof, the customary excipients, for example lactose, talc, silicic acid, aluminium hydroxide, calcium silicate and polyamide powder, or mixtures of these substances. Sprays can additionally contain the conventional propellants, such as chlorofluorohydrocarbons. Topical formulations are believed to be particularly well suited for treating inflammation (discussed further below), in which case the topical formulation can contain, for example, between about 5 and about 20 percent, by weight.

In addition to the above, generally non-active components of the above-described formulations, these formulations can include other active materials, particularly, actives which have been identified as useful in the treatment of prostate, lung, stomach, breast, colon, pancreatic cancers and/or other adenocarcinomas. These actives can be broad-based anticancer agents, such that they also are useful in treating other types of cancers (i.e., in addition to adenocarcinomas) or they may be more specific, for example, in the case where the other active is useful for treating adenocarcinomas or particular types of adenocarcinomas. The other actives can also have non-anti-cancer pharmacological properties in addition to their anti-andenocarcinoma properties. For example, the other actives' can have anti-inflammatory properties, or, alternatively, they can have no such anti-inflammatory properties.

It will be appreciated that the actual preferred amount of MM soft tissues or extracts thereof to be administered according to the present invention will vary according to the particular MM soft tissue or extract thereof, the particular composition formulated, and the mode of administration. Many factors that may modify the action of the MM soft tissue or extract thereof (e.g., body weight, sex, diet, time of administration, route of administration, rate of excretion, condition of the subject, drug combinations, and reaction sensitivities and severities) can be taken into account by those skilled in the art. For example, suitable daily doses for oral administration of MM extracts can range from about 1 mg/kg to about 300 mg/kg. Administration can be carried out continuously or periodically within the maximum tolerated dose. Optimal administration rates for a given set of conditions can be ascertained by those skilled in the art using conventional dosage administration tests.

The present invention, in yet another aspect thereof, relates to a method of inhibiting the activity of 5-lipoxygenase or 12-lipoxygenase or both in cells. The method includes contacting a sample comprising the cells with a composition comprising an MM soft tissue or an extract thereof. The methods of this aspect of the present invention can be practiced in vitro or in vivo.

More particularly, the method of the present invention can be used in vivo to treat a subject suffering from a disease or condition associated with excessive 5-lipoxygenase activity or 12-lipoxygenase activity or both. Such diseases or conditions are meant to include, for example, inflammation, arthritis, skin diseases, asthma, multiple sclerosis, diabetes, coronary disease, and combinations thereof. In the case where the method of the present invention is carried out in vivo, for example, where the cells having excessive 5-lipoxygenase and/or 12-lipoxygenase activity are present in a human subject, contacting can be carried out by administering a therapeutically effective amount of the MM soft tissue or extract thereof to the human subject. Details with regard to administering MM soft tissues or extracts thereof in accordance with the method of this aspect of the present invention are the same as those discussed above with regard to the treatment of subjects afflicted with adenocarcinomas.

The present invention is further illustrated with the following examples.

EXAMPLES

Example 1

Isolation and Extraction of Soft Tissues from MM

Two hundred pounds of MM were obtained by dragging. The MM individuals were heated in boiling water or approximately 15 minutes, and the shells were removed from the MM by hand. The resulting MM pieces were then frozen and subsequently freeze-dried. Some MM pieces were 'slow-heat' dried after water heating in a traditional fish drier. Dried pieces from all drying methods were finely divided by grinding, and the resulting powder was industrially extracted with standard alcohol solvents. Some individual MM pieces were extracted with diethyl ether, and some of the powder was extracted with liquid propane. Each of the extraction processes yielded reddish-green oils in amounts of approximately 10-15% of the dry weight of the powder.

Example 2

Isolation and Extraction of Specific Soft Tissues from MM and Analysis of Extracts After water heating and deshelling, the resulting MM whole pieces were cooled, and the greenish liver portions were cut out of and separated from the remainder of the soft tissues. Each of the liver portion and the soft tissue remainder portion was separately frozen, freeze-dried, ground to powder, and extracted with standard alcohol solvents. The oil which resulted from extraction of the liver portion was green in color and is hereinafter referred to as MMG. The oil which resulted from extraction of the soft tissue remainder portion was red in color and is hereinafter referred to as MMR. MMG was analyzed as containing the following fatty acids in the following percentages (by weight):

| | |
|---|---|
| 12-methyltetradecanoic acid | <0.01 |
| C08:0 octanoic (caprylic) acid | 0.13 |
| C10:0 decanoic (capric) acid | 0.07 |
| C11:0 undecanoic (hendecanoic) acid | <0.01 |
| C12:0 dodecanoic (lauric) acid | 0.50 |
| C14:0 tetradecanoic (myristic acid) | 2.66 |
| C14:1 tetradecenoic (myristoleic) acid | <0.01 |
| C15:0 pentadecanoic acid | 0.28 |
| C15:1 pentadecenoic acid | <0.01 |
| C16:0 hexadecanoic (palmitic) acid | 8.16 |
| C16:1 hexadecenoic (palmitoleic) acid | 6.92 |
| C16:2 hexadecadienoic acid | <0.01 |
| C16:3 hexadecatrienoic acid | <0.01 |
| C16:4 hexadecatetraenoic acid | <0.01 |
| C17:0 heptadecanoic (margaric) acid | 0.05 |
| C17:1 heptadecenoic (margaroleic) acid | <0.01 |
| C18:0 octadecanoic (stearic) acid | 1.13 |
| C18:1 octadecenoic (oleic) acid | 2.53 |
| C18:2 octadecadienoic (linoleic) acid | 1.38 |
| C18:3 octadecatrienoic (linolenic) acid | 0.13 |

-continued

| | |
|---|---|
| C18:4 octadecatetraenoic acid | <0.01 |
| C19:0 nonadecanoic acid | <0.01 |
| C20:0 eicasanoic (arachidic) acid | <0.01 |
| C20:1 eicasenoic (gadoleic) acid | 0.49 |
| C20:2 eicasadienoic acid | 0.23 |
| C20:3 eicasatrienoic acid | 0.07 |
| C20:4 eicasatetraenoic (arachidonic) acid | <0.01 |
| C20:5 eicasapentaenoic acid | 0.96 |
| C21:0 heneicasanoic acid | <0.01 |
| C21:5 heneicasapentaenoic acid | <0.01 |
| C22:0 docosanoic (behenic) acid | <0.01 |
| C22:1 docosenoic (erucic) acid | 0.19 |
| C22:2 docosadienoic acid | <0.01 |
| C22:3 docosatrienoic acid | <0.01 |
| C22:4 docosatetraenoic acid | <0.01 |
| C22:5 docosapentaenoic acid | 0.19 |
| C22:6 docosahexaenoic acid | 0.20 |
| C24:0 tetracosanoic (lignoceric) acid | <0.01 |
| C24:1 tetracosenoic (nervonic) acid | 0.09 |

Example 3

Effect of MMG and MMR on 5-Lipoxygenase Pathway

The inhibitory actions of MMG and MMR on the synthesis of leukotriene and 5-HETE by human neutrophils were studied as follows.

Human neutrophils were prepared from blood taken from normal volunteers. The blood was drawn, and it was anticoagulated with 2 ml of 4.5% EDTA in water per each 10 ml of blood. A further 2 ml of 6.0% Dextran T500 was added to each of the resulting 12 ml blood/EDTA mixtures, and the resulting solution was placed in a water bath at 37° C. to sediment the red blood cells. Following sedimentation, the supernatant was carefully laid over a double gradient of Percoll (the densities of the lower and upper Percoll layers being 1.092 and 1.070, respectively), and the layered product was spun at 500 g for 35 minutes. The neutrophil cells ("PMN") at the lower interface and down to the red cell layer were collected, diluted at least 3-fold with $Ca^{2+}/Mg^{2+}$-free Dulbecco's phosphate buffer, and centrifuged at 600 g for 10 minutes. Following centrifugation, the supernatant was carefully aspirated, and the pellet was vigorously mixed with 1 ml of $Ca^{2+}/Mg^{2+}$-free Dulbecco's phosphate buffer by rapid aspiration/deaspiration into a 1 ml plastic disposable pipette. A further 40 ml of $Ca^{2+}/Mg^{2+}$-free Dulbecco's phosphate buffer was then added and mixed by inversion. The cell suspension was then centrifuged at 600 g for 10 minutes. Following centrifugation, the supernatant was removed and the PMN pellet lysed with 10 ml of a 0.2% cold sodium chloride solution for 20 seconds. 10 ml of a 1.6% cold sodium chloride solution was then added, and the mixture was centrifuged at 600 g for 10 minutes. The resulting PMN pellet was vigorously mixed with 1 ml of Hank's buffer by rapid aspiration/deaspiration into a 1 ml plastic disposable pipette and then finally suspended in Hank's buffer at $2.7 \times 10^6$ PMN (as measured using a Coulter counter), in preparation for the leukotriene/5-HETE assay.

The PMN leukotriene pathway was activated as follows. 1 ml of PMN suspension ($3.4 \times 10^6$ PMN/ml) was transferred to a 13 ml glass tube (chromic acid washed) and placed in a water bath at 37° C. for 5 minutes prewarming. Following prewarming, at time zero, 10 µl of MMG in methanol was added to quadruplicate tubes over a 20 second period. A second set of quadruplicate tubes was prepared using MMR in place of the MMG, and a third set of quadruplicate tubes was prepared using an equivalent volume of methanol as control in place of the MMG. At 7 minutes, 5 ml of 2 mM arachidonic acid (10 µM final) was added, over 20 seconds, to each of the four tubes in each set. At 11 minutes, 5 ml of 1 mM calcium ionophore (A23187) was added, over 20 seconds, to each of the four tubes in each set. At 16 minutes, the reaction was terminated by the addition of 100 µl of 100 mM citric acid. This lowers the pH of the aqueous phase to less than 3 which is necessary for the extraction of the leukotrienes into the organic phase. After checking the pH of the several samples to ensure a pH of less than 3, 40 ng of Prostaglandin $B_2$ ("$PGB_2$") and 166 ng of 15-HETE were added to each tube as the internal standard for $LTB_4$ and 5-HETE, respectively, and the samples were mixed. $LTB_4$ standard curves (in the standard curve range of 0 to 50 ng) and 5-HETE standard curves (in the standard curve range of 0 to 250 ng) were generated by adding 1 ng/µl of $LTB_4$ and 5 ng/µl of 5-HETE to tubes containing 1 ml PMN, 100 µl of 100 mM citric acid, and 40 ng $PGB_2$ and 166 ng 15-HETE. All tubes were then vortexed, 5 ml of chloroform/methanol (7:3) was added, the tubes were again vortexed vigorously for 30 seconds, and the tubes were then centrifuged for 10 minutes at 2000 rpm. Approximately 3.5 ml of the lower chloroform layer (containing the extracted leukotrienes, HETES, and internal standards) was transferred to a 3 ml borosilicate glass tube, and the chloroform was evaporated in a Savant centrifugal evaporator at room temperature under vacuum. The samples were then reconstituted in 100 µl of the $LTB_4$ mobile phase (67% methanol, 33% $H_2O$, 8% acetic acid (pH adjusted to 6.2 with ammonium hydroxide)), and the reconstituted mixture was vortexed and transferred to Waters low volume (typically <25 µl) inserts for injection. The HPLC was set up (flow rate: 1 ml/min; column: $C_{18}$ Nova Pak), and all samples were assayed for $LTB_4$ and all trans isomers of $LTB_4$ (at 270 nm) and for 5-HETE (at 235 nm). Retention times for $PGB_2$, 6-trans-$LTB_4$, 6-trans-epi-$LTB_4$, and $LTB_4$ were 5.9 min, 8.8 min, 9.9 min, and 12.3 min, respectively. The results of the study are presented in Table I. The values in Table I represent the amounts (in ng, expressed as mean±SD) of 6-trans-$LTB_4$, 6-trans-epi-$LTB_4$, $LTB_4$, and 5-HETE produced per $10^6$ PMN in the presence of MMG, in the presence of MMR, and in the absence of both MMG and MMR (control). The results show that, compared with methanol control, both MMG and MMR inhibit the production of each of 6-trans-$LTB_4$, 6-trans-epi-$LTB_4$, $LTB_4$, and 5-HETE.

TABLE I

| Compound | Methanol Control | MMR (1:10,000 dilution) | MMG (1:10,000 dilution) |
|---|---|---|---|
| 6-trans-$LTB_4$ | 19.2 ± 1.1 | 9.2 ± 0.4 | 3.7 ± 0.3 |
| 6-trans-epi-$LTB_4$ | 18.1 ± 0.8 | 7.9 ± 0.5 | 2.5 ± 0.2 |
| $LTB_4$ | 12.6 ± 0.3 | 7.8 ± 0.2 | 7.5 ± 0.2 |
| 5-HETE | 178 ± 11 | 133 ± 2 | 69 ± 2 |

The studies were repeated using different samples of MMG and MMR. The results of these studies are set forth in Table II. The results show that, compared with methanol control, MMG inhibits the production of each of 6-trans-$LTB_4$, 6-trans-epi-$LTB_4$, $LTB_4$, and 5-HETE, and MMR inhibits the production of 5-HETE.

TABLE II

| Compound | Methanol Control | MMR (1:10,000 dilution) | MMG (1:10,000 dilution) |
|---|---|---|---|
| 6-trans-$LTB_4$ | 17.2 ± 1.5 | 14.8 ± 1.0 | 5.9 ± 0.8 |
| 6-trans-epi-$LTB_4$ | 15.2 ± 1.4 | 12.7 ± 0.9 | 3.4 ± 0.7 |
| $LTB_4$ | 9.9 ± 0.5 | 8.9 ± 0.6 | 5.3 ± 0.7 |
| 5-HETE | 173 ± 9 | 133 ± 4 | 69 ± 15 |

Example 4

Effect of MMG and MMR on the 12-Lipoxygenase Pathway

The inhibitory actions of MMG and MMR on the synthesis of 12-HETE by human platelets were studied as follows.

80 ml of blood was taken from a normal volunteer, and the blood was anticoagulated with ACD (1 ml ACD per 9 ml of blood). The anticoagulated blood was spun for 10 minutes at 100 g (800 rpm). The plasma layer containing platelets was removed, and each 15 ml was placed in a 50 ml conical polypropylene tube. To each tube, 35 ml of platelet washing solution (90 mM sodium chloride, 5 mM potassium chloride, 5 mM glucose, and 36 mM citric acid) was added. The tubes were then centrifuged for 15 minutes at 1000 g (2000 rpm), and the tubes were washed again with platelet washing solution and centrifuged again for 15 minutes at 1000 g (2000 rpm). The platelets were resuspended in approximately 1 ml of Hank's buffered salt solution and manually counted using a haemocytometer, and the platelet count was adjusted to $7.8 \times 10^8$ platelets/ml for use in the 12-HETE synthesis studies.

Platelet 12-HETE synthesis was activated as follows. 1 ml of platelet suspension ($74 \times 10^6$ platelets/ml) was transferred to a 13 ml glass tube (chromic acid washed) and placed in a water bath at 37° C. for 5 minutes prewarming. Following prewarming, at time zero, 10 µl of MMG in methanol was added to quadruplicate tubes over a 20 second period. A second set of quadruplicate tubes was prepared using MMR in place of the MMG, and a third set of quadruplicate tubes was prepared using an equivalent volume of methanol as control in place of the MMG. At 8 minutes, 5 ml of 2 mM arachidonic acid (10 µM final) was added, over 20 seconds, to each of the four tubes in each set. At 13 minutes, 5 ml of 1 mM calcium ionophore (A23187) (5 µM final) was added, over 20 seconds, to each of the four tubes in each set. At 18 minutes, the reaction was terminated by the addition of 100 µl of 100 mM citric acid. This lowers the pH of the aqueous phase to less than 3 which is necessary for the extraction of 12-HETE into the organic phase. After checking the pH of the several samples to ensure a pH of less than 3, 166 ng of 15-HETE were added to each tube as the internal standard for 12-HETE, and the samples were mixed. 12-HETE standard curves (in the standard curve range of 0 to 250 ng) were generated by adding 5 ng/µl of 5-HETE to the tubes. 4.5 ml of chloroform/methanol (7:3) was added, the tubes were vortexed vigorously for 30 seconds, and the tubes were then centrifuged for 10 minutes at 1000 g (2000 rpm). Approximately 3.5 ml of the lower chloroform layer (containing 12-HETE and 5-HETE) was transferred to a 3 ml borosilicate glass tube, and the chloroform was evaporated in a Savant centrifugal evaporator at 30° C. under vacuum. The samples were then reconstituted in 100 µl of the 12-HETE mobile phase (77% methanol, 23% $H_2O$, 8% acetic acid (pH adjusted to 6.2 with ammonium hydroxide)), and the reconstituted mixture was vortexed and transferred to Waters low volume (typically <25 μl) inserts for injection. The HPLC was set up (flow rate: 1 ml/min; column: $C_{18}$ Nova Pak), and all samples were assayed for 12-HETE (at 235 nm). Retention times for 12-HETE and 5-HETE were 7.5 min and 9.2 min, respectively. The results of the study are presented in Table III. The values in Table III represent the amounts (expressed as a percentage of the methanol control) (mean ±SD) of 12-HETE produced in the presence of MMG, in the presence of MMR, and in the absence of both MMG and MMR (control). The results show that, compared with methanol control, both MMG and MMR inhibit the production of 12-HETE.

TABLE III

| Compound | Methanol Control | MMR (1:10,000 dilution) | MMG (1:10,000 dilution) |
|---|---|---|---|
| 12-HETE | 100 ± 9 | 65 ± 3 | 39 ± 5 |

Example 5

Effect of MMG and MMR on Pancreatic Cancer Cell Proliferation

The effect of MMG and MMR on the proliferation of two malignant human pancreatic cancer cell lines (AsPC-1 and PANC-1) were studied as follows. Cells from each of the two cell lines were treated under serum-free conditions with MMG at various dilutions (1:2000, 1:4000, 1:8000, 1:160000, and 1:32000, based on the crude MMG oil extract) and with control (which contained no MMG). Proliferation of the cells was then measured by incorporation of radiolabeled thymidine into cellular DNA. The results, presented in FIG. 1A (AsPC-1) and 1B (PANC-1), show that MMG causes a concentration-dependent inhibition of proliferation of both pancreatic cancer cell lines. The experiment was repeated using MMR in place of MMG. The results, presented in FIGS. 1C (AsPC-1) and 1D (PANC-1), show that MMR also causes a concentration-dependent inhibition of proliferation of both pancreatic cancer cell lines.

Example 6

Effect of MMG and MMR on Pancreatic Cancer Cell Morphology

Figure 2B:
Figure 2C:
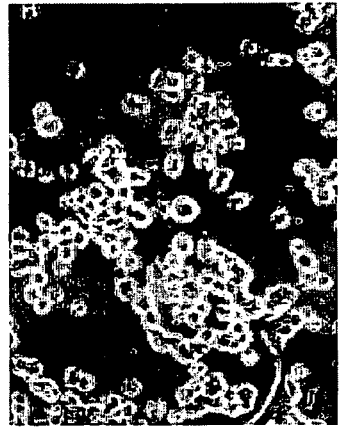
Figure 2D:
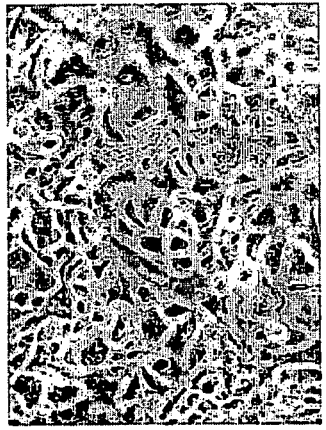
Figure 2E:
Figure 2F:
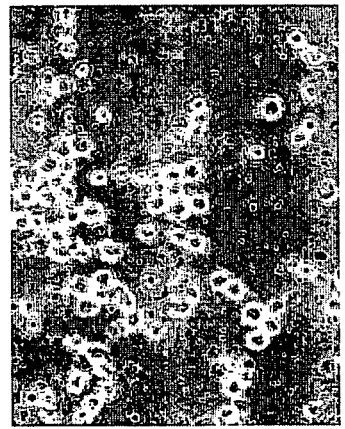

AsPC-1 and PANC-1 pancreatic cells were separately treated under serum free conditions with a 1:400 dilution of MMG. Phase-contrast microscopy revealed marked morphological changes in treated AsPC-1 and PANC-1 pancreatic cancer cells (FIGS. 2C and 2F, respectively) compared with non-treated controls (FIGS. 2A and 2D). Over time, the treated cells became rounded and exhibited membrane blebbing and nuclear condensation. These morphological changes have been previously interpreted as reflecting apoptosis. Similar results were seen when AsPC-1 and PANC-1 pancreatic cells were separately treated under serum free conditions with a 1:800 dilution of MMR, as shown in FIG. 2B (AsPC-1) and in FIG. 2E (PANC-1).

Example 7

TUNEL Assay

Figure 3A:
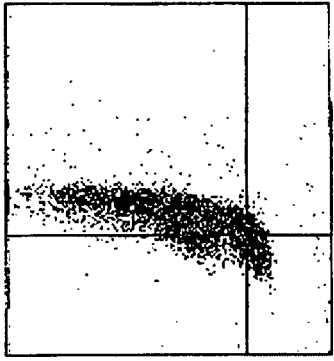
FIGS. 3B and 3C are dot plots showing TUNEL assay results of AsPC-1 pancreatic cancer cells treated with two different MM oil extracts compared to control (FIG. 3A).
FIGS. 3E and 3F are dot plots showing TUNEL assay results of PANC-1 pancreatic cancer cells treated with two different MM oil extracts compared to control (FIG. 3D). The increases (relative to controls) of fluorescence events in the upper right quadrants of the samples treated with MM oil extracts are due to UTP labeling of fragmented DNA.
Figure 3B:
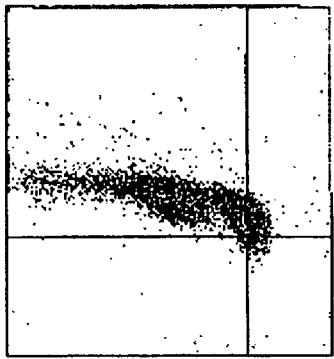
Figure 3C:
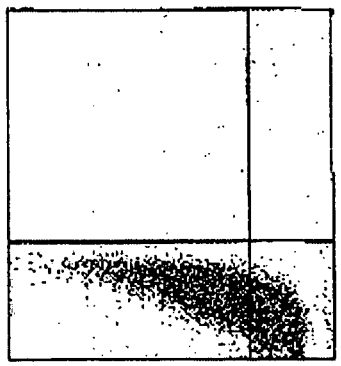
Figure 3D:
Figure 3E:
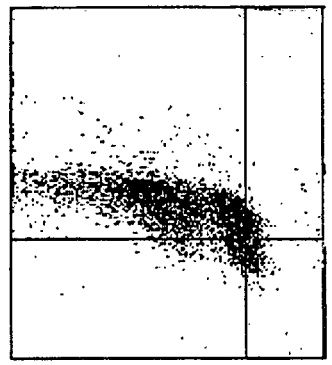
Figure 3F:
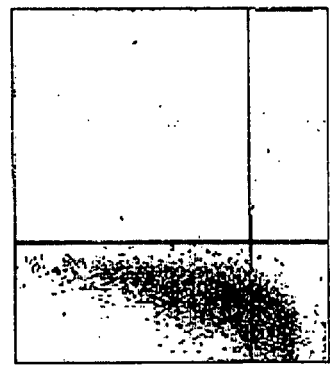

Apoptosis was measured by flow cytometry using a terminal deoxynucleotidyl transferase-mediated deoxyuridine triphosphate nick-end labeling ("TUNEL") assay. AsPC-1 and PANC-1 cells were treated with MMG or MMR or control for a period of time, then digested with trypsin-EDTA, washed with ice-cold PBS twice, and fixed in 10% paraformaldehyde on ice for 20 minutes. Cells were then washed with PBS, permeabilized with 70% ethanol for at least 4 hours, washed again with PBS, and incubated with 2.5 units of terminal deoxynucleotidyl transferase (TdT enzyme) and 100 pmol Br-dUTP in DNA labeling solution for one hour at 37° C. Cells were then rinsed twice, resuspended in 0.1 ml fluorescein labeled anti-BrdU antibody solution in the dark for 30 minutes. Then, 0.5 ml propidium iodide/RNase A solution was added, and the cells analyzed by flow cytometry at 488 nm excitation. Treatment of AsPC-1 and PANC-1 cells with diluted MMG greatly increased apoptosis relative to control. The results are presented in FIGS. 3A-3C for AsPC-1 cells, where an increase, relative to control (FIG. 3A), of fluorescence events in the upper right quadrant seen in the MMR-treated sample (FIG. 3B) and in the MMG-treated sample (FIG. 3C) is due to UTP labeling of fragmented DNA, which confirms apoptosis in the AsPC-1 cell line. For the experiments with PANC-1 cells, the results are presented in FIGS. 3D-3F, where an increase; relative to control (FIG. 3D), of fluorescence events in the upper right quadrant seen in the MMR-treated sample (FIG. 3E) and in the MMG-treated sample (FIG. 3F) is due to UTP labeling of fragmented DNA, which confirms apoptosis in the PANC-1 cell line.

Example 8

Effect of MMG/MMR on Growth of Pancreatic Tumors In Hamsters

Figure 4:
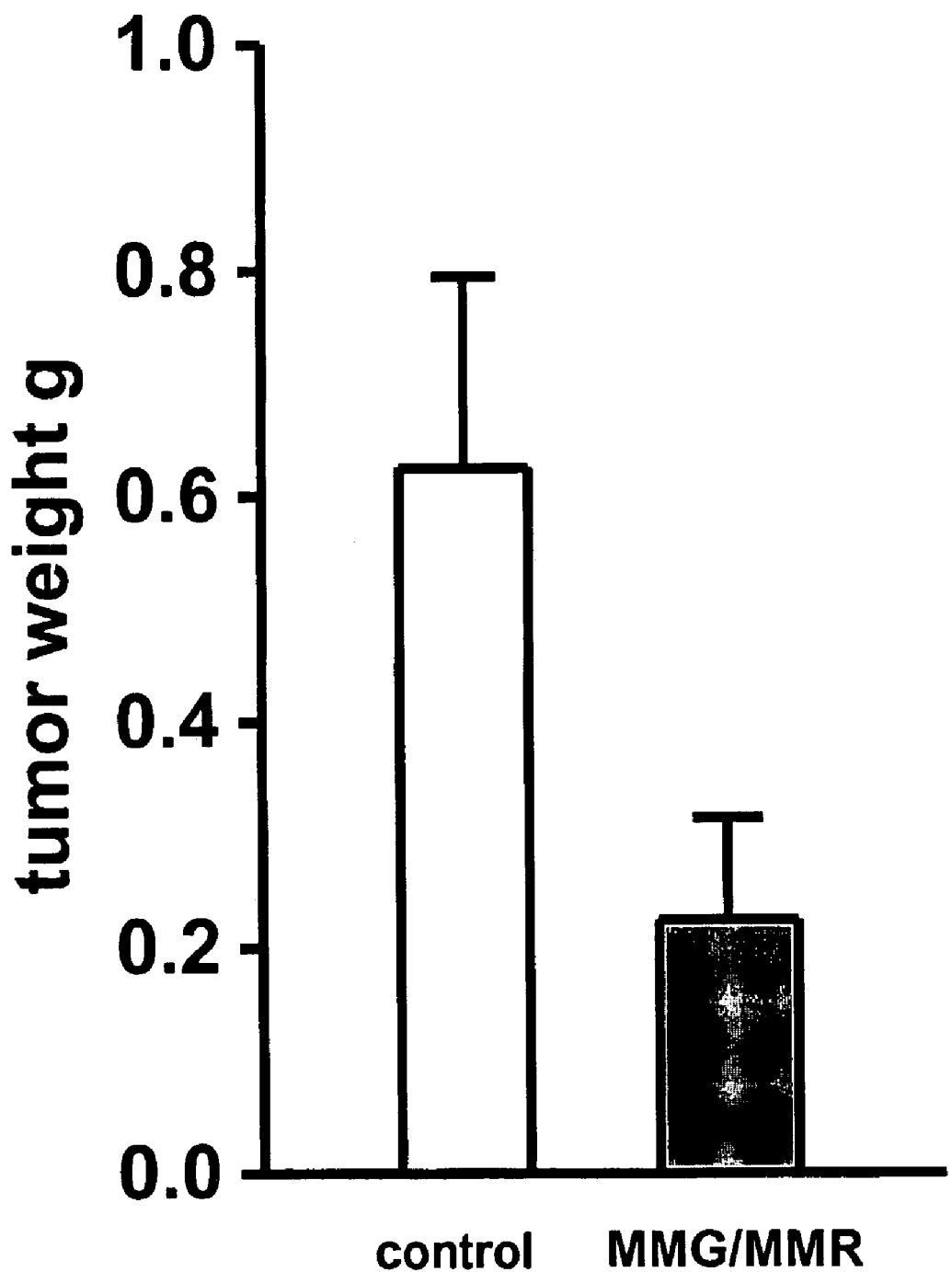
FIG. 4 is a bar graph showing the effect of dietary MM oil extract on tumor weight in hamsters into which malignant hamster pancreatic cancer was orthotopically transplanted.

The effect of adding a combination of MMG and MMR to the diet on growth of orthotopically transplanted malignant hamster pancreatic cancers in hamsters was studied as follows. Tumor cells (3 million/animal) were injected directly into the splenic lobe of each hamster's pancreas. The hamsters were fed with a semisynthetic hamster chow to which a combination of MMG and MMR was added at 1% of total weight. Corn oil (1%) was added to the diet of the control hamsters. After 28 days all hamsters were euthanized and autopsied. Tumors were found in 9/10 control hamsters but only in 6/10 hamsters fed with the MMG/MMR-supplemented diet. More importantly, average tumor size and weight in MMG/MMR-treated animals were less than one-third of those in control animals. A bar graph showing the effect of MMG/MMR in the diet on tumor weight is presented in FIG. 4. Furthermore, two of the control animals, but none of the MMG/MMR-treated animals, had metastatic disease, with the tumor invading lymph nodes and liver.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed is:
1. A composition comprising:
   an oil isolated from *Modiolus modiolus* or isolated from a portion of *Modiolus modiolus*, wherein said oil is isolated from *Modiolus modiolus* liver.
2. A composition according to claim 1, wherein said composition further comprises:
   a pharmaceutically acceptable excipient.

3. A composition according to claim 1, wherein said composition further comprises:
a nutriceutically acceptable excipient.

4. A composition comprising:
an isolated soft tissue from *Modiolus modiolus* or an oil isolated from *Modiolus modiolus* or isolated from a portion of *Modiolus modiolus*; and
a pharmaceutically or nutriceutically acceptable excipient, wherein said composition comprises an oil isolated from *Modiolus modiolus* or isolated from a portion of *Modiolus modiolus*.

5. A composition according to claim 4, wherein said oil is produced by a method comprising contacting *Modiolus modiolus* or a portion thereof with a solvent under conditions effective to extract one or more oils from the *Modiolus modiolus* or portion thereof.

6. A composition according to claim 5, wherein said oil is produced by a method comprising contacting an isolated *Modiolus modiolus* soft tissue with a solvent under conditions effective to extract one or more materials from the isolated *Modiolus modiolus* soft tissue.

7. A composition according to claim 6, wherein the isolated *Modiolus modiolus* soft tissue is selected from the group consisting of *Modiolus modiolus* foot, heart, stomach, kidney, gonad, liver, mouth, labial palps, gills, and combinations thereof.

8. A composition according to claim 6, wherein the isolated *Modiolus modiolus* soft tissue is *Modiolus modiolus* liver.

9. A composition according to claim 6, wherein the isolated *Modiolus modiolus* soft tissue comprises *Modiolus modiolus* liver and wherein the isolated *Modiolus modiolus* soft tissue is substantially free of *Modiolus modiolus* foot, heart, stomach, kidney, gonad, mouth, labial palps, and gills.

10. A composition according to claim 6, wherein the isolated *Modiolus modiolus* soft tissue is selected from the group consisting of *Modiolus modiolus* foot, heart, stomach, kidney, gonad, mouth, labial palps, gills, and combinations thereof and wherein the isolated *Modiolus modiolus* soft tissue is substantially free of *Modiolus modiolus* liver.

11. A composition according to claim 5, wherein the solvent is selected from the group consisting of an alcohol solvent, an ether solvent, an hydrocarbon solvent, a halohydrocarbon solvent, an aromatic solvent, carbon dioxide, and combinations thereof.

12. A composition comprising:
an isolated soft tissue from *Modiolus modiolus* or an oil isolated from *Modiolus modiolus* or isolated from a portion of *Modiolus modiolus*; and
a pharmaceutically or nutriceutically acceptable excipient, wherein said composition comprises an oil isolated from *Modiolus modiolus* or isolated from a portion of *Modiolus modiolus* and a pharmaceutically acceptable excipient.

13. A composition comprising:
an isolated soft tissue from *Modiolus modiolus* or an oil isolated from *Modiolus modiolus* or isolated from a portion of *Modiolus modiolus*; and
a pharmaceutically or nutriceutically acceptable excipient, wherein said composition comprises an oil isolated from *Modiolus modiolus* or isolated from a portion of *Modiolus modiolus* and a nutriceutically acceptable excipient.

\* \* \* \* \*